(12) United States Patent
Santoli et al.

(10) Patent No.: US 6,716,425 B1
(45) Date of Patent: Apr. 6, 2004

(54) METHOD OF PREVENTING CANCER RECURRENCE

(75) Inventors: Daniela Santoli, Bryn Mawr, PA (US); Giovanni Rovera, Bryn Mawr, PA (US); Alessandra Cesano, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 728 days.

(21) Appl. No.: 08/879,422

(22) Filed: Jun. 20, 1997

Related U.S. Application Data

(63) Continuation-in-part of application No. 08/472,686, filed on Jun. 6, 1995, now Pat. No. 5,702,702.

(51) Int. Cl.[7] .............................. A01N 63/00; C12N 5/08

(52) U.S. Cl. .................. 424/93.71; 424/93.1; 424/93.7; 435/325; 435/366; 435/372; 435/372.3

(58) Field of Search ............................... 424/93.1, 93.7, 424/93.71; 435/325, 366, 372, 372.3

(56) References Cited

U.S. PATENT DOCUMENTS

| | | | |
|---|---|---|---|
| 5,166,059 A | 11/1992 | Paston et al. | 435/69.7 |
| 5,272,082 A | 12/1993 | Santoli et al. | 435/372.3 |

OTHER PUBLICATIONS

A. Cesano et al, "Antitumor Efficacy of a Human Major Histocompatibility Complex Nonrestricted Cytotoxic T–Cell Line (TALL–104) in Immunocompetent Mice Bearing Syngeneic Leukemia", *Cancer Research*, 56:4444–4452 (Oct. 1, 1996).

A. Cesano et al, "Phase I Clinical Trial with a Human Major Compatibility Complex Nonrestricted Cytotoxic T–Cell Line (TALL–104) in dogs with Advanced Tumors", *Cancer Research*, 56:3021–3029 (Jul. 1, 1996).

A. Cesano et al, "Effects of Lethal Irradiation and Cyclosporin A Treatment on the Growth and Tumoricidal Activity of a T Cell Clone Potentially Useful in Cancer Therapy", *Cancer Immunol. Immunother.*, 40:139–151 (Mar. 1995).

A. Cesano et al, "Reversal of Acute Myelogenous Leukemia in Humanized SCID Mice Using a Novel Adoptive Transfer Approach", *J. Clin. Invest.*, 94:1076–1084 (Sep. 1994).

A. Cesano et al, "Synergistic Effects of Adriamycin and TALL–104 Cell Therapy Against a Human Gastric Carcinoma in Vivo", *Anticancer Research*, 17:1887–1892 (May-Jun. 1997).

A. Cesano et al, "Toxicological and Immunological Evaluation of the MHC–non–restricted Cytotoxic T Cell Line TALL–104", *Cancer Immunol. Immunother.*, 44:125–136 (May 1997).

S. Visonneau et al, "Cell Therapy of a Highly Invasive Human Breast Carcinoma Implanted in Immunodeficient (SCID) Mice", *Clinical Cancer Research*, 3:1491–1500 (Sep. 1997).

S. Visonneau et al, "Successful Treatment of Canine Malignant Histocytosis with the Human Major Histocompatibility Complex Nonrestricted Cytotoxic T–Cell Line TALL–104", *Clinical Cancer Research*, 3:1789–1797 (Oct. 1997).

(List continued on next page.)

*Primary Examiner*—Ronald B. Schwadron
(74) *Attorney, Agent, or Firm*—Howson and Howson

(57) ABSTRACT

Methods for treating cancer in a mammalian patient having cancer and a functional immune system, and for preventing recurrences of cancer following completion of cancer therapy, are described. The methods involve administration of a course of therapy with modified TALL-104 cells, without requiring the co-administration of an immunosuppressive agent.

12 Claims, 2 Drawing Sheets-

OTHER PUBLICATIONS

S. Chan et al, "Mechanisms of Interferon–γ Induction by Natural Killer Cell Stimulatory Factor (NKSF): Role of Transcription and mRNA Stability in the Synergistic Interactions Between NKSF and Interleukin–2", *J. Immunol.,* 148(1):92–98 (Jan. 1, 1992).

D. Santoli et al, "Synergistic and Antagonistic Effects of IL–1α and IL–4, Respectively, on the IL–2–Dependent Growth of a T Cell Receptor–γδ+Human T Leukemia Cell Line", *J. Immunol.,* 144(12):4703–4711 (Jun. 15, 1990).

R. O'Connor et al, "Growth Factor–Dependent Differentiation Along the Myeloid and Lymphoid Lineages in an Immature Acute T Lymphocytic Leukemia", *J. Immunol.,* 145(11):3779–3787 (Dec. 1, 1990) [O'Connor I].

R. O'Connor et al, "Growth Factor Requirements of Childhood Acute T–Lymphoblastic Leukemia: Correlation Between Presence of Chromosomal Abnormalities and Ability to Grow Permanently in Vitro", *Blood,* 77(7):1534–1545 (Apr. 1, 1991).

A. Cesano et al, "Homing and Progression Patterns of Childhood Acute Lymphoblastic Leukemias in Severe Combined Immunodeficiency Mice", *Blood,* 77(11):2463–2474 (Jun. 1, 1991).

A. Cesano et al, "Establishment of a Karyotypically Normal Cytotoxic Leukemic T–Cell Line from a T–All Sample Engrafted in SCID Mice", *Blood,,* 81(10):2714–2722 (May 15, 1993).

A. Cesano et al, "Effect of Human Interleukin 3 on the Susceptibility of Fresh Leukemia Cells to Interleukin–2–Induced Lymphokine Activated Killing Activity", *Leukemia,* 6(6):567–573 (Jun. 1992).

A Cesano et al, "Cytokine Modulation of the Susceptibility of Acute T–Lymphoblastic Leukemia Cell Lines to LAK Activity", *Leukemia,* 7(3):404–409 (Mar. 1993).

A. Cesano et al, "Mechanisms of MHC–Non–Restricted Lysis in Two Human Killer T Cell Lines", *Nat. Immun.,* 11(5):288–289 (Oct. 1992).

A. Cesano et al, "Two Unique Human Leukemia T–Cell Lines Endowed with a Stable Cytotoxic Function and a Different Spectrum of Target Reactivity Analysis and Modulation of Their Lytic Mechanisms", *In Vitro Cell Dev. Biol.,* 28A:648–656 (Sep.–Oct. 1992).

A. Cesano et al, "Inducible Expression of Granulocyte–Macrophage Colony–Stimulating Factor, Tumor Necrosis Factor–α, and Interferon–γ in Two Human Cytotoxic Leukemic T–Cell Lines", *In Vitro Cell Dev. Biol.,* 28A:657–662 (Sep.–Oct. 1992).

A Cesano et al, "The Severe Combined Immunodeficient (SCID) Mouse as a Model for Human Myeloid Leukemias", *Oncogene,* 7:827–836 (May 1992).

A Cesano et al, "Treatment of Experimental Glioblastoma with a Human Major Histocompatibility Complex Nonrestricted Cytotoxic T Cell Line", 55:96–101 (Jan. 1, 1995).

A. Cesano et al, "An Effective and Safe Marrow Purging Strategy Using a Lethally Irradiated Killer T Cell Clone", in *Advances in Bone Marrow Purging and Processing,* Fourth International Symposium, pp. 165–173 (Oct. 1994).

A. Cesano et al, "Cellular and Molecular Mechanisms of Activation of MHC Nonrestricted Cytotoxic Cells by IL–12", *J. Immunology,* 151:2943–2957 (Sep. 1993).

P. Greenberg et al, "Effector Mechanisms Operative in Adoptive Therapy of Tumor–Bearing Animals: Implications for the Use of Interleukin–2", *J. Biol. Resp. Modifiers,* 3(5):455–461 (1984).

J. Klarnet et al, "Helper–Independent CD8+ Cytotoxic T Lymphocytes Express IL–1 Receptors and Require IL–1 for Secretion of IL–2", *J. Immunol.,* 142(7):2187–2191 (Apr. 1, 1989).

M. Cheever et al, "Potential Uses of Interleukin 2 in Cancer Therapy", *Immunobiol.,* 172:365–382 (1986).

"First AIDS Gene–Transfer Clinical Comes Before RAC", *Biotechnology Newswatch,* 11(22):1–3 (Nov. 18, 1991).

"RAC Phases Out Human Gene Therapy Unit; Approves Six New Protocols" *Biotechnology Newswatch,* 12(4):9–10 (Feb. 17, 1992).

D. Ojcius et al, "Cell–Mediated Killing: Effector Mechanisms and Mediators", *Cancer Cells,* 2(5):138–145 (May 1990).

E. Grimm et al, "Lymphokine–Activated Killer Cell Phenomenon: Lysis of Natural Killer–Resistant Fresh Solid Tumor Cells by Interleukin 2–Activated Autologous Human Peripheral Blood Lymphocytes", *J. Exp. Med.,* 155:1823–1841 (Jun. 1982).

A. Rosenberg, "Lymphokine–Activated Killer Cells: A New Approach to Immunotherapy of Cancer", *J. Natl. Can. Inst.,* 75(4):595–603 (Oct. 1985).

S. Rosenberg et al, "Special Report—Observations on the Systemic Administration of Autologous Lymphokine–Activated Killer Cells and Recombinant Interleukin–2 to Patients with Metastatic Cancer", *New Engl. J. Med.,* 313(23):1485–1492 (Dec. 5, 1985).

S. Rosenberg et al, "A Progress Report on the Treatment of 157 Patients with Advanced Cancer Using Lymphokine–Activated Killer Cells and Interleukin–2 or High–Dose Interleukin–2 Alone", *New Engl. J. Med.,* 316(15):889–897 (Apr. 9, 1987).

S. Rosenberg, "What's New in General Surgery: The Development of New Immunotherapies for the Treatment of Cancer Using Interleukin–2", *Ann. Surg.,* 208(2):121–135 (Aug. 1988).

S. Rosenberg et al, "Experience with the Use of High–Dose Interleukin–2 in the Treatment of 652 Cancer Patients", *Ann. Surg.,* 210(4):474–485 (Oct. 1989).

M. Rosenstein et al, "Lymphokine–Activated Killer Cells: Lysis of Fresh Syngeneic Natural Killer–Resistant Murine Tumor Cells by Lymphocytes Cultured in Interleukin–2", *Cancer Res.,* 44:1946–1953 (May 1984).

J. Mule et al, "Adoptive Immunotherapy of Established Pulmonary Metastases with LAK Cells and Recombinant Interleukin–2", *Science,* 225:1487–1489 (Sep. 28, 1984).

R. Lafreniere et al, "Successful Immunotherapy of Murine Experimental Hepatic Metastases with Lymphokine–Activated Killer Cells and Recombinant Interleukin 2", *Cancer Res.,* 45:3735–3741 (Aug. 1985).

A. Mazumder et al, "Successful Immunotherapy of Natural Killer–Resistant Established Pulmonary Melanoma Metastases by the Intravenous Adoptive Transfer of Syngeneic Lymphocytes Activated in vitro by Interleukin 2", *J. Exp. Med.,* 159:495–507 (Feb. 1984).

W. West et al, "Constant–Infusion Recombinant Interleukin–2 in Adoptive Immunotherapy of Advanced Cancer", *New Engl. J. Med.,* 316(15):898–905 (Apr. 9, 1987).

S. Topalian et al, "Expansion of Human Tumor Infiltrating Lymphocytes for use in Immunotherapy Trials", *J. Immunol. Meth.,* 102:127–141 (1987).

K. Itoh et al, "Interleukin 2 Activation of Cytotoxic T–Lymphocytes Infiltrating into Human Metastatic Melanomas", *Cancer Res.,* 46:3011–3017 (Jun. 1986).

R. Lee et al, "Cardiorespiratory Effects of Immunotherapy with Interleukin–2", *J. Clin. Oncol.,* 7(1):7–20 (Jan. 1989).

M. Lotze et al, "Mechanisms of Immunologic Antitumor Therapy: Lessons from the Laboratory and Clinical Applications", *Hum. Immunol.,* 28:198–207 (1990).

J. Gootenberg et al, "A Biochemical Variant of Human T Cell Growth Factor Produced by a Cutaneous T Cell Lymphoma Cell Line", *J. Immunol.,* 129(4):1499–1505 (Oct. 1982).

S. Arya et al, "T–Cell Growth Factor Gene: Lack of Expression in Human T–Cell Leukemia–Lymphoma Virus–Infected Cells", *Science,* 223:1086–1087 (Mar. 1984).

Y. Kaufmann et al, "Interleukin 2 Induces Human Acute Lymphocytic Leukemia Cells to Manifest Lymphokine–Activated–Killer (LAK) Cytotoxicity", *J. Immunol.,* 139(3):977–982 (Aug. 1, 1987).

A. Kasid et al, "Human Gene Transfer: Characterization of Human Tumor–Infiltrating Lymphocytes as Vehicles for Retroviral–Mediated Gene Transfer in Man", *Proc. Natl. Acad. Sci. USA,* 87:473–477 (Jan. 1990).

N. Nishihara et al, "Augmentation of Tumor Targeting in a Line of Glioma–Specific Mouse Cytotoxic T–Lymphocytes by Retroviral Expression of Mouse–γInterferon Complementary DNA", *Cancer Research,* 48:4730–4735 (Sep. 1, 1988).

H. Karasuyama et al, "Autocrine Growth and Tumorigenicity of Interleukin 2–Dependent Helper T Cells Transfected with IL–2 Gene", *J. Exp. Med.,* 169:13–25 (Jan. 1989).

T. Torigoe et al, "Interleukin 4 Inhibits IL–2–Induced Proliferation of a Human T–Leukemia Cell Line without Interfering with p56–LCK Kinase Activation", *Cytokine,* 4(5):369–376 (Sep. 1992).

T. Torigoe et al, "Interleukin–3 Regulates the Activity of the LYN Protein–Tyrosine Kinase in Myeloid–Committed Leukemic Cell Lines", *Blood,* 80(3):617–624 (Aug. 1, 1992).

B. Perussia et al, "Natural Killer (NK) Cell Stimulatory Factor or IL–12 has Differential Effects on the Proliferation of TCR–αβ$^+$, TCR–γδ$^+$ T Lymphocytes, and NK Cells", *J. Immunol.,* 149(11):3495–3502 (Dec. 1, 1992).

B. Lange et al, "Pediatric Leukemia/Lymphocyte with t(8;14) (q24;q11)", *Leukemia,* 6(7):613–618 (Jul. 1992).

T. Han et al, "Stimulating Capacity of Blast Cells from Patients with Chronic Myelocytic Leukaemia, in Blastic Crisis in 'One–Way' Mixed Lymphocyte Reaction: Lack of Evidence for T Lymphoblastic Conversion", *Immunology,* 35:299–305 (1978).

B. Rouse et al, "Consequences of Exposure to Ionizing Radiation for Effector T Cell Function In Vivo", *Viral Immunology,* 2(2):69–78 (1989).

A. Stern et al, "Purification to Homogeneity and Partial Characterization of Cytotoxic Lymphocyte Maturation Factor from Human B–Lymphoblastoid Cells", *Proc. Natl. Acad. Sci. USA,* 87:6808–6812 (Sep. 1990).

K. Foon, "Biological Response Modifiers: The New Immunotherapy", *Cancer Research,*49, 1621–1639 (Apr. 1989).

T. Boon, "Tumor Antigens Recognized by Cytolytic T Lymphocytes: Present Prespectives for Specific Immunotherapy" *Int. J. Cancer,* 54:177–180 (Jan. 1993).

M. Osband et al., "*Problems in the Investigational Study and Clinical Use of Cancer Immunotherapy*" *Immunology Today,* 11: 402–404 (1990).

J. Mule et al., "Immunotherapy with Lymphokine Combinations", *Important Adv. In Oncol.,* 10:99–126 (1989).

A. Cesano et al., "Use of Lethally Irradiated Major Histocompatibility Complex Nonrestricted Cytotoxic T–Cell Line for Effective Purging of Marrows Containing Lysis–Sensitive or Resistant Leukemic Targets", *Blood,*87:393–403 (Jan. 1, 1996).

METHOD OF PREVENTING CANCER RECURRENCE

This application is a continuation-in-part of U.S. patent application Ser. No. 08/472,686, filed Jun. 6, 1995, now U.S. Pat. No. 5,702,702.

FIELD OF THE INVENTION

The invention relates generally to the treatment of cancers, and more specifically to methods which prevent recurrence of cancer.

BACKGROUND OF THE INVENTION

Adoptive transfer therapy for the treatment of cancer has been described. One such method makes use of a lethally irradiated human T cell line (TALL-104), (CD3/TCRαβ+ CD8+CD16−) [A. Cesano et al, In Vitro Cell. Dev. Biol., 28A:648 (1992); A. Cesano et al, J. Immunol., 151:2943–2957 (1993); and A. Cesano et al, Cancer Immunol. Immunoth., 40:139 (1995)], which is endowed with MHC non-restricted killer activity against a broad range of tumors across several species, while sparing cells from normal tissues.

To date, the use of this TALL-104 cell line in such adoptive transfer has been described as requiring an immunosuppressed patient. For example, use of this cell has been described in studies in immunodeficient and immunocompetent murine models with transplantable tumors and in canines with spontaneously arising cancers [A. Cesano et al, J. Clin. Invest., 94:1076 (1994); A. Cesano et al, Cancer Res., 55:96 (1995); A. Cesano et al, Cancer Res., 56:3021 (1996); and A. Cesano et al, Cancer Res., 56:4444–4452 (1996)]. The latter two publications describe the administration of cyclosporin A to pharmacologically immunosuppress the cancer patient, to avoid rejection of the allogeneic TALL-104 effector cells.

Improved methods of treating cancers are needed in the art, and particularly methods in which a patient can receive a therapeutic anti-cancer agent without additionally receiving an immunosuppressive agent.

SUMMARY OF THE INVENTION

The invention provides a method of treating cancer, and particularly, for preventing recurrence of cancer. This method involves the step of administering an effective amount of modified TALL-104 cells to a mammalian cancer patient in the absence of an immunosuppressive agent. This first administration step may be repeated as needed, desirably for a selected number of consecutive days or one to two days following the previous administration. Optionally, a booster may be administered approximately one month following the completion of the course of treatment. Desirably, the patient undergoes therapy with the method of the invention following completion of conventional cancer therapy.

Other aspects and advantages of the present invention are described further in the following detailed description of the preferred embodiments thereof.

DETAILED DESCRIPTION OF THE INVENTION

Figure 1:
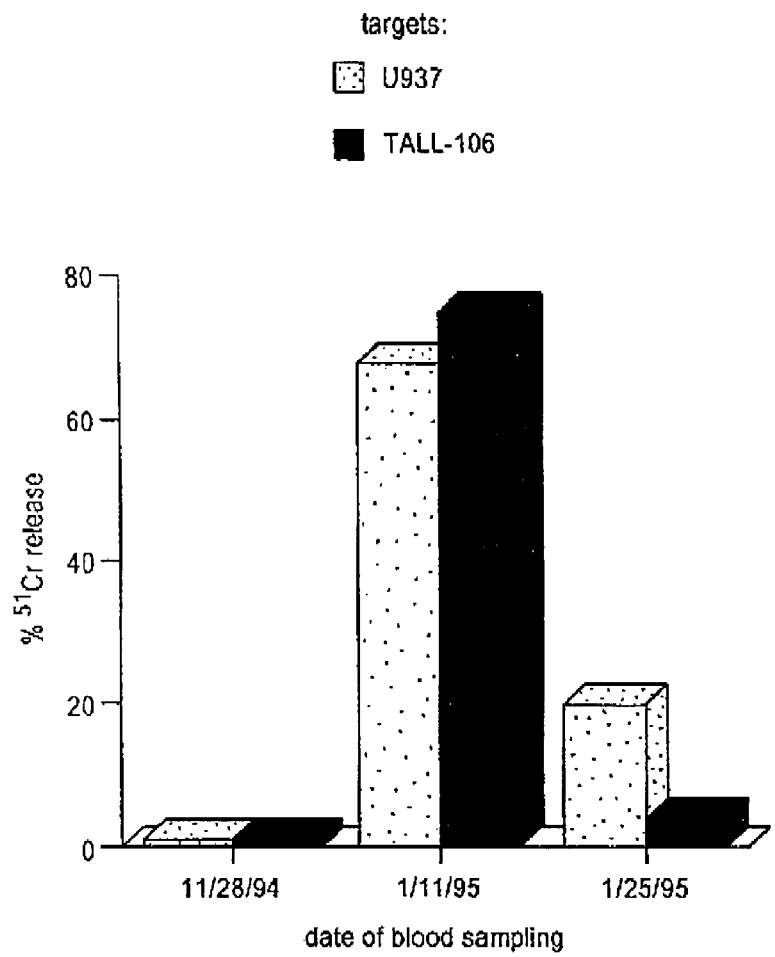
FIG. 1 is a bar chart illustrating the cytotoxic activity of canine patient "P.B.K."'s peripheral blood mononuclear cells (PBMC) against NK-sensitive (U937) and NK-resistant (TALL-106) target cells. PBMC were separated from blood samples obtained immediately before the first TALL-104 cell infusion (Nov. 28, 1994), on the day of regression of relapsed subcutaneous lesions (Jan. 11, 1995), and 2 weeks later (Jan. 25, 1995). Effector-to-target ratio= 50:1.

The present invention provides a method of preventing relapse or recurrence of disease in mammalian patients, including both human and veterinary patients, particularly those previously treated for cancer. The inventors have found that modified TALL-104 cells induce an anti-tumor specific (i.e., vaccine-like) immune response in the treated patient. This results in effective elimination of residual disease by the patient's immune system in the absence of additional chemotherapy. This effect is present even when the modified TALL-104 cells are administered in the absence of an immunosuppressive agent.

Thus, the invention provides a method of preventing relapse in mammalian cancer patients by administering a course of therapy with modified TALL-104 cells, preferably in the absence of an immunosuppressive agent. In a currently preferred embodiment, the method of the invention is performed following completion of the patient's surgery, chemotherapy, radiation therapy, or other course of treatment for eradication of the cancer, many of which are known to those of skill in the art. Such cancer therapies may involve the administration of modified TALL-104 cells in the presence of an immunosuppressive agent, as described in U.S. patent application Ser. No. 08/472,686, filed Jun. 6, 1995, now U.S. Pat. No. 5,702,702. Alternatively, the cancer therapy may involve administration of modified TALL-104 cells in combination with a course of chemotherapy, as described in U.S. patent Ser. No. 08/847,000, filed May 1, 1997, now U.S. Pat. No. 6,022,538. These co-pending, co-owned patent applications are incorporated by reference herein. In another embodiment, the method of the invention may also be used as the primary cancer therapy. See, Examples 3–7 below.

According to the present invention, the method of the invention may begin immediately (e.g., 1 day to about one week) following completion of cancer therapy, or may be delayed pending confirmation that the patient's cancer is in remission (e.g., about one week to six months following completion of conventional cancer treatment). However, timing of the administration of modified TALL-104 cells according to the method of the invention may be readily adjusted by one of skill in the art depending upon other factors, including, for example, the patient's condition following completion of the primary cancer therapy. Suitable dosage regimens, including modes and routes of administration and cell doses, are discussed below.

As discussed above, the method of the invention utilizes modified TALL-104 cells, which are derived from a TALL-104 cell line and are preferably modified by lethal γ-irradiation as described below. The unmodified TALL-104 cells are available from the American Type Culture Collection, 10801 University Boulevard, Manassas, Va. 20110-2209 as Accession No. CRL 11386. This deposit of these cells was made on Jun. 15, 1993 and the cells and are described in U.S. Pat. No. 5,272,082.

TALL-104 cells may be modified in such a way as to provide them with an increased cytotoxicity against tumor and virus-infected targets. Such modification methods have been described in detail in International Patent Publication No. WO94/26284, published Nov. 24, 1994, which is incorporated by reference herein. For example, one modification step includes in vitro treatment of the TALL-104 cells with a selected cytokine or combination of cytokines. For example, the two interleukins, recombinant human (rh) interleukin (IL) IL-2 and rhIL-12, when used independently to treat the cell line, induce the cell line's cytotoxic activity. When these cytokines are used together to modify the cell line, the modified cell line displays additive or increased cytotoxic effects. This results in a significant increase in cytotoxic activity and recycling capability, ultimately leading to 100% elimination of tumor targets at an E:T ratio <0.1:1 [Cesano et al, *J. Immunol.*, 151:2943 (1993)].

Another modification step involves the exposure of the TALL-104 cell line to lethal irradiation to confer irreversible loss of growth capability with full retention of cytotoxic activity, both in vitro and in vivo. This is achieved by subjecting the cell lines to γ-irradiation just prior to their use. Preferably, the cells are irradiated at 4000 rads using a $^{137}Cs$ source.

As described in International Patent Publication No. WO94/26284, irradiation of TALL-104 cells provides a modified cytotoxic cell line that has lost its proliferative ability and, therefore, the possibility of growing in an unrestrained fashion in the recipient organism. In fact, unlike their non-irradiated counterparts, modified γ-irradiated TALL-104 cells of this invention transplanted into SCID mice do not cause leukemia.

Preferably, modified TALL-104 cells are prepared as follows. TALL-104 cells (ATCC CRL 11386) are exponentially grown in tissue culture in the presence of recombinant human (rh) IL-2. If desired, IL-12 can be added for about 18 hours before use to enhance the killing activity of the cell line. The cytokine-treated TALL-104 cells are then γ-irradiated, preferably at about 4,000 rads. The resulting cell line is referred to as the modified TALL-104 cell line.

According to the method of this invention for administering modified TALL-104 cells without immunosuppressive agents, dosage regimens may be readily adjusted taking into account such factors as the route of administration, the type of cancer being treated, and the stage of the disease and the condition of the patient, as needed. Generally, between about $10^6$ to about $10^8$, and more preferably between $10^7$ to about $10^8$, of the modified TALL-104 cells are suspended in a suitable amount of a pharmaceutically acceptable carrier and administered daily for the desired length of time by an appropriate route. One particularly desirable carrier is saline. Another desirable carrier is plasma protein fraction 5% with 10% DMSO. However, other suitable carriers are well known to those of skill in the art. The selection of the carrier is not a limitation on the present invention.

The cells may be administered by injection, e.g., intravenously, intradermally, by direct site injection, intraperitoneally, intranasally, or the like. Currently, the preferred route of administration for such cancers as lymphomas and malignant histiocytosis, and other solid tumors is intravenous. However, where desired or necessary, the modified TALL-104 cells may be administered locally, i.e., to the site of the targeted tumor, or to a specific organ. For example, the TALL-104 cells may be delivered via a shunt to the liver for liver cancer, or directly to the affected area of the brain for glioblastomas and other brain tumors (e.g., medulloblastomas, astrocytomas, and the like). Generally, where the modified TALL-104 cells are administered locally, the amount of cells administered in a single or repeated dosage is considerably lower than the range provided above. For example, treatment of blastoma may require local administration of only $10^9$ cells over the course of a week.

Administration of TALL-104 cells may be repeated as needed. As one example, modified TALL-104 cells may be administered daily for five consecutive days, and a booster administered after approximately one month. In another example, the modified TALL-104 cells are administered every other day over the course of two weeks, with cell boosts administered monthly for a desired period of time, e.g., six months. Such boosts may be administered for one to two consecutive days at the doses set forth above. However, the timing, dosage and course of administration and determination as to the number and timing of boosters desired may be readily determined by one of skill in the art. The timing and the mode of administration do not limit the present invention.

The examples below show that treatment of a mammalian veterinary cancer patient with modified TALL-104 cells is capable of achieving specific anti-tumor immunity. For example, the achievement of a durable complete remission (CR) in a dog (P.B.K.) with very advanced disease upon systemic TALL-104 cell infusion was as unexpected as was the regression of his relapsed nodules after completion of cell therapy. See, Example 4. The regression of relapsed nodules is indicative of the development of a state of specific anti-tumor immunity in the animal that protected him from further relapses throughout his life span. Immunological studies of P.B.K.'s blood samples before, during, and after cell therapy showed the appearance of MHC non-restricted cell-mediated cytotoxicity against human tumor cells (both NK-sensitive and -resistant) during TALL-104 therapy, with a peak response at the time of regression of the relapsed nodules. The same pattern of responses were seen in the other three dogs treated.

These examples illustrate the preferred methods of the invention. These examples are illustrative only and do not limit the scope of the invention.

EXAMPLE 1

Induction of Specific Anti-tumor Immunity by TALL-104 Cells in Immunocompetent Mice Bearing Syngeneic Leukemia The TALL-104 cells were modified as follows. The cells were exponentially grown in tissue culture in the presence of IL-2. Before use, the cells were washed, incubated overnight in the presence of IL-2 (100 U/ml) and/or IL-12 and γ-irradiated using a Cesium source with gamma rays (4000 rads).

Anti-tumor efficacy and induction of a state of specific anti-tumor immunity was observed upon administration of TALL-104 cells (prepared as described above) in B6D2F1 mice bearing syngeneic leukemia. As in the experiments described immediately above, the 7OZ pre-B ALL cell line was used.

7OZ cells could be detected in the mouse tissues by PCR amplification of their specific CDRIII region: specifically, they were detectable in the bone marrow (BM) as early as 2 days after 7OZ cell transfer, in the peripheral blood (PB) starting from day 3, and in most organs including the central nervous system starting from day 5.

At different stages of leukemic infiltration (day 0, 2, 3, 5), mice were immunosuppressed with CsA (10 mg/Kg i.p.), and IL-2-treated, irradiated TALL-104 cells were injected ($2 \times 10^7$ i.p.) on alternate days for a total of 5 times.

The results obtained showed that modified TALL-104 cell treatment was able to completely prevent or reverse 7OZ cell growth in the animals, depending on the time of initiation of therapy (early versus advanced stages, respectively). Mice that were still asymptomatic after 6 months were also disease free at the molecular level, as shown by PCR.

Importantly, rechallenge of these animals with high doses of 7OZ cells ($2 \times 10^7$ i.p.) did not result in leukemia, indicating the ability of their immune system to recognize and reject the original tumor cells. It therefore appears that the IL-2-stimulated, gamma-irradiated TALL-104 cells were not only able to cause disease regression in these animals, but also to induce a specific state of anti-tumor immunity. This finding indicates that upon TALL-104 cell treatment, the host can be protected against relapses due to residual disease through the activation of his own immune cells.

EXAMPLE 2

Anti-tumor Efficacy of TALL-104 Cells in Canines With Spontaneous Refractory Tumors Recent experiments in dogs with spontaneous refractory (end-stage) tumors have revealed both the safety and efficacy of the use of cytokine (IL-2) stimulated, irradiated TALL-104 cells in veterinary practice. The following example is provided below in which treatment with TALL-104 cells cured a dog with cancer and induced a permanent anti-tumor immunity by activating the dog's immune cells against his own tumor.

An 8-year-old Scottish Terrier presented with end-stage malignant histiocytosis. The prognosis was grave due to the progressive disease and lack of response to chemotherapeutics. Prior to TALL-104 treatment, the dog had several large lymph nodes, and had developed left inguinal and right axillary lymphadenopathy.

After the dog was treated with 6 infusions of IL-2-stimulated, gamma-irradiated TALL-104 cells ($10^8$ cells/kg) on alternate days, the right axillary lymph node had completely regressed. At this time, the dog demonstrated significant improvement in overall attitude and well-being. Objective and measurable anti-tumor effects were observed after two more treatments, with complete regression of the axillary lymph node and >50% decrease in the inguinal lymph nodes and neck mass. Thoracic radiographs were negative for lymphadenopathy or pulmonary infiltrate. CBC and chemscreen were normal throughout the treatment course. TALL-104 therapy was ended at this point.

Two weeks later, new subcutaneous nodules were found upon reexamination on the left hind and front legs (2.0 cm) of the dog. It was decided to surgically remove these nodules to test their susceptibility to TALL-104 cell lysis in $^{51}$Cr-release assays. However, 2 days later, the lesions had spontaneously regressed and surgical removal was not possible.

Blood was drawn and Ficoll-Hypaque-separated lymphocytes were tested for natural killer (NK) activity against human tumor targets, including TALL-104 cells. Results showed that the dog's lymphocytes were highly activated, being able to kill both NK-susceptible (U937) and NK-resistant (T-ALL) human targets. Interestingly, however, his PBL failed to lyse TALL-104 cells, indicating lack of specific cytotoxic T lymphocyte (CTL) responses against the xenogeneic effectors.

When blood was drawn again 10 days later, NK activity had significantly declined. The overall in vitro data indicated the presence of an activated immunological state in the dog at the time of spontaneous regression of the metastatic lesions, which could explain its ability to fight against relapses without further treatments. No previous tumor biopsies were available from the dog to test tumor-specific CTL activity. Continued improvement was observed later on with complete regression of the earlier lesions. This dog remained in complete remission throughout his life span (14 months), and died of a disease unrelated to cancer, as documented both clinically and with histopathology at necropsy.

Examples 1 and 2 demonstrate that passive treatment with TALL-104 cells induces an anti-tumor specific immune response in the treated patient similar to that expected in response to a vaccine. This results in effective elimination of residual disease by the patient's immune system in the absence of additional chemotherapy.

Treatment with TALL-104 cells therefore can complement cancer treatment with conventional chemotherapeutic agents and may even reduce the amount of chemotherapy a patient will require in the treatment of a cancer. Additionally the anti-tumor effect of TALL-104 administration also appears to be effective with cancers which are, or have become, resistant to at least some types of chemotherapy.

EXAMPLE 3

TALL-104 Cell Administration to Dogs With Malignant Histiocytosis (MH)

This example and those which follow show the ability of systemically delivered TALL-104 cells to induce durable clinical remissions in four out of four dogs with malignant histiocytosis (MH). The animals received multiple intravenous injections of lethally irradiated (40 Gy) TALL-104 cells at the dose of $10^8$ cells/kg, with (2 dogs) or without (2 dogs) cyclosporin A, followed by monthly boosts. No significant clinical or laboratory toxicities developed during cell therapy; interestingly, a strong correlation was found between the dogs' clinical and immunological responses. One dog with advanced disease (intrathoracic involvement) refractory to chemotherapy, achieved a complete remission (CR) within 2 months from the first TALL-104 cell infusion. This dog died 14 months later for unrelated causes: histological analysis of his organs post-mortem revealed no evidence of neoplasia, thus confirming the achievement of CR also at the pathological level. The other three dogs with MH, who presented with multiple subcutaneous and cutaneous lesions and lymphadenopathy, but no visceral involvement, were treated with TALL-104 cells as single agent (no chemotherapy was administered). Two of these dogs achieved a CR soon after cell therapy and the third dog had 2 long-lasting partial responses; CR in this dog was later achieved by combined administration of chemotherapy and cell therapy. Remarkably, none of the three dogs who received cell therapy at diagnosis developed visceral disease in 4–76 months follow-up, despite the documented aggressiveness of this malignancy. The durable clinical responses experienced by all 4 MH cases upon TALL-104 cell therapy indicate the high responsiveness of this fatal canine tumor to the xenogeneic effectors and their strong therapeutic potential even in hosts with heavy tumor burden.

The results of this study are reported in Examples 4–8 below.

A. Diagnosis With MH

Four dogs diagnosed with MH were treated with TALL-104 cells at the Veterinary Oncology Services in West Chester, Pa., starting in November 1994. The diagnosis of malignant histiocytosis in all four dogs was made based on clinical and morphologic criteria and on confirmation of the histiocytic lineage of tumor cells by immunohistochemical staining [positive staining for the histiocytic markers α-1-antitrypsin, cathepsin B, and lysozyme, but no reactivity for Leu-M1, a myelomonocytic marker (not shown)].

Sections (6 μm) of paraffin blocks from the dogs' tumor lesions were stained with hematoxylin and eosin (HE) for histological analysis. Immunohistochemical staining was done using the avidin-biotin-peroxidase complex method [S. M. Hsu et al., *J. Histochem. Cytochem.*, 29: 577–580 (1981)). Briefly, sections were deparaffinized, dehydrated through graded alcohol and washed in 0.01M PBS, pH 7.4. To block nonspecific binding, sections were incubated with normal horse serum (1:75; Vector Laboratories, Burlingame, Calif.) for 20 min followed by overnight incubation at 4° C. with primary antibodies anti-lysozyme (1:200), α-1-trypsin (1:300, Dako Corp., Carpinteria, Calif.), anti-cathepsin B (1:300, ICN Biochemicals, Costa Mesa, Calif.), and Leu M-1 (1:150, Becton-Dickinson, Mountain View, Calif.). Normal mouse serum was used as control antibody. Sections were incubated in biotinylated horse anti-mouse IgG (1:200, Vector Laboratories) for 45 minutes. All incubations were done in a humidified chamber at room temperature. 3-amino-9-ethylcarbazole (Sigma Chemical Co., St. Louis, Mo.) was used as chromogen, and sections were counterstained with Mayer's hematoxylin.

The clinical characteristics of these patients at the beginning of cell therapy are summarized in Table 1.

TABLE 1

Characteristics of the MH dogs treated with TALL-104 cell therapy

| Canine patient | Sex/Age/Breed | Previous therapy | Clinical stage at cell therapy initiation |
|---|---|---|---|
| P.B.K. | M/8/Scottish Terrier | Five cycles of chemotherapy with doxorubicin, cyclophosphamide, vincristine, dacarbazine, L-asparaginase | Multiple cutaneous and subcutaneous lesions, metastatic lymphoadenopathy, intrathoracic involvement |
| F.C. | M/7/West Highland Terrier | None | Multiple cutaneous and subcutaneous lesions, metastatic lymphoadenopathy |
| M.G. | F/3/Bernese Mountain Dog | None | Cutaneous and subcutaneous lesions around |

TABLE 1-continued

Characteristics of the MH dogs treated with TALL-104 cell therapy

| Canine patient | Sex/Age/Breed | Previous therapy | Clinical stage at cell therapy initiation |
|---|---|---|---|
| | | | muzzle; metastatic lymphoadenopathy |
| S.S. | F/1/Golden Retriever | None | Cutaneous and subcutaneous lesions around muzzle; metastatic lymphoadenopathy |

P.B.K. was enrolled in the study in 1994: at the time of diagnosis he had advanced disease with skin, lymph nodes, and intrathoracic involvement [A. Cesano, et al., *Cancer Res.*, 56: 3021–3029 (1996)]. Although P.B.K. had originally responded to chemotherapy with a CR, progressive disease developed and decreased cardiac contractibility precluded further treatment with doxorubicin. The other three dogs (M.G., F.C., S.S.) that entered the TALL-104 cell study in 1995 and 1996 were newly diagnosed cases with disease limited to skin and lymph nodes: because of their less advanced stage and of the dramatic response to TALL-104 cell therapy seen in P.B.K., these three dogs were not given chemotherapy and were treated with TALL-104 cells as single agent according to the protocol set forth below.

B. Large-scale Expansion of TALL-104 Cells for Therapy

TALL-104 cells were grown in endotoxin-free Iscove's modified Dulbecco's medium (Gibco-BRL, Grand Island, N.Y.) supplemented with 10% heat-inactivated fetal bovine serum (Sigma) and 100 U/ml rhIL-2 (Chiron Therapeutics, Emeryville, Calif.) in a humidified incubator at 37° C with 10% $CO_2$ in T-175 vented cap flasks (Falcon, Franklin Lakes, N.J.). Mycoplasma contamination was monitored weekly on cell samples from ten randomly chosen flasks using a commercial PCR kit (ATCC, Rockville, Md.). At the time of therapy, cells were harvested, centrifuged in 250 ml conical centrifuge tubes (Corning, New York, N.Y.), washed twice in saline (Abbott Lab, King of Prussia, Pa.), resuspended in 100 ml saline, γ-irradiated (40 Gy) using a $^{137}Cs$ source, and transferred to a blood transfer pack (Baxter Diagnostics, Inc., Glendale, Pa.) for systemic administration within 2 to 4 hours from irradiation. Cell aliquots were removed from the bag for determination of cytotoxic activity and sterility (quality control assays).

C. Protocols of TALL-104 Cell Administration

Table 2 summarizes the schedule of TALL-104 cell infusions received by each dog in the study. Cells were γ-irradiated (40 Gy) and administered at the dose of $10^8$/kg in saline as an i.v. bolus over 30 min. Cell boosts were given at the indicated intervals and consisted of 2 consecutive days of TALL-104 cell injections ($10^8$/kg, i.v.). The immunosuppressive drug CsA (Sandimmune, Sandoz, East Hanover, N.J.) was administered to P.B.K. and F.C. at a dose of 10 mg/kg per os once a day, starting from the day before the first TALL-104 cell administration throughout the 2 weeks of treatment. In the boosts phase, CsA was given to P.B.K. and F.C. only on the day before and on the same day of the two TALL-104 cell injections. Because CsA did not prevent the development of humoral responses to TALL-104 cells (see below) the dogs treated in 1996 (M.G. and S.S.) were not given CsA in association with cell therapy. Except for P.B.K., who was part of a phase 1 study (13) and received TALL-104 cells on alternate days for 2 weeks after chemotherapy, the other three dogs who were treated with single-agent TALL-104 cells received a more aggressive cell treatment consisting in one or two cycles of cells administered for 5 consecutive days (Table 2).

TABLE 2

Protocols of TALL-104 cell administration to dogs with MH

| Canine patient | Date of cell therapy initiation | Schedule | Number of boosts | CsA(10 mg/kg) |
|---|---|---|---|---|
| P.B.K. | Nov. 28, 1994 | every other day for 2 weeks | 2 (weekly) | Yes |
| F.C. | Aug. 21, 1995 | daily for 5 days, 2-week rest, daily for 5 days | 12 (monthly) | Yes |
| M.G. | Jan. 16, 1996 | daily for 5 days | 15 (monthly) | No |
| S.S. | Sep. 1, 1996 | daily for 5 days, weekend rest, daily for 5 days | 4 (monthly) | No |

D. Toxicity Monitoring

Clinical signs of acute toxicity (such as fever, chills, hypotension, diarrhea, vomiting) were monitored during and after each cell injection. All dogs were treated as outpatients during the course of TALL-104 cell therapy and the owners were properly instructed to report on the well-being of their pets during therapy. Blood and serum samples (for CBC counts, serum chemistry, cytotoxicity assays, cytokine production and immunological monitoring, see below) were obtained from the patients before the study, immediately before each TALL-104 cell administration, and throughout the follow-up period.

E. Cytotoxicity Assays

PBMC were isolated from heparinized blood samples by Accu-Prep (Accurate Chemical, Westbury, N.Y.) lymphocyte gradient centrifugation and tested as effectors in an 18-h $^{51}$Cr-release assay against the human leukemic target cell lines U937 and K562 (both NlC-sensitive) and TALL-106 (NK-resistant). This test was routinely used to monitor the possible development of MHC non-restricted cellular immune responses against human (xenogeneic) cells. Briefly, a fixed number of $^{51}$Cr-labeled target cells ($10^4$/well) was tested against four effector cell concentrations, as described [R. O'Conner et al, *Blood*, 77:1534–1545 (1991); A. Cesano and D. Santoli, *In Vitro Cell Biol.*, 28A:648–656 (1992)]. Percent specific $^{51}$Cr-release was calculated from the mean of three replicates.

F. Cytokine Assays

The presence of IFN-γ, TNF-α, GM-CSF, and TNF-α in serum samples collected pre-study, and throughout cell therapy was tested using cytokine-specific ELISA kits (Endogen, Boston, Mass.) according to the manufacturer's instructions. The sensitivity of the assay was 20 pg/ml for IFN-γ and TNF-α, 8 pg/ml for TNF-β, and 7.8 pg/ml for GM-CSF.

G. Immunological Monitoring

Immunological studies were performed on serum samples and PBMC (pre-study, before each TALL-104 cell injection, and during the follow-up period) to monitor the possible development of TALL-104-specific humoral and cellular immune responses, respectively. Sera were diluted 10:3 in FACS buffer (PBS without $Ca^{2+}$ and $Mg^{2+}$, 0.1% $NaN_3$, 2% IgG-free horse serum) and transferred to wells of a 96-well round-bottom plate (Falcon). FACS buffer was used as negative control. TALL-104 cells were washed once in FACS buffer and added to the plates at $10^5/50)\mu l$/well. Sera and cells were incubated for 1 hour at room temperature. After three more washes, fluorescein isothiocyanate-conjugated rabbit anti-canine IgG (whole molecule) (Sigma) was added at a dilution of $2\times10^{-2}$ for 1 hour at 4° C. At the end of the incubation, cells were washed, resuspended in 150 μl FACS buffer and analyzed by flow cytometry using an Ortho Cytofluorograph cell sorter.

To monitor the development of TALL-104-specific cellular immune response, PBMC samples were tested against $^{51}$Cr-labeled TALL-104 cells in an 18-hour $^{51}$Cr-release assay, as described above.

H. PCR Analysis

Peripheral blood samples from the dogs were obtained immediately before each TALL-104 cell infusion and at various intervals during and after cell therapy; DNA was extracted from the PBMC and frozen [A. Cesano et al., *Cancer Res.*, 56: 3021–3029 (1996)]. The presence of circulating TALL-104 cells in each cell extract was evaluated by PCR analysis using two primers specific for the human mini-satellite region YNZ.22 [S. Mackinnon et al., *Blood*, 21: 3235–3241 (1992)]. An oligonucleotide probe recognizing 24 nucleotides in the middle of the amplified sequence was used to demonstrate the specificity of the PCR products by Southern blot hybridization, as described [Mackinnon et al, cited above].

EXAMPLE 4

Clinical Responses to TALL-104 Cell Therapy

Table 3 summarizes the clinical responses observed in the four dogs with MH upon TALL-104 cell therapy (updated to June, 1997).

TABLE 3

Clinical responses to TALL-104 cell treatment in dogs with MH

| Canine patient | Clinical response[a] | Duration | Outcome |
|---|---|---|---|
| P.B.K | CR | 14 months | Died of causes unrelated to cancer |
| F.C | First PR | 2 months | |
| | Second PR | 6 months | |
| | CR[c] | 4 months | NED[b] |
| M.G. | CR | 16 months+ | NED |
| S.S. | CR | 9 months+ | NED |

[a]CR, complete response; PR, partial response.
[b]No evidence of disease.
[c]The CR in F.C. was achieved upon combined chemotherapy/cell therapy.

At the time of initiation of cell therapy, P.B.K. presented with prefemoral and left inguinal enlarged lymph nodes and right axillary lymphadenopathy, and his performance status was poor (MKPS=2). After 2 weeks of systemic TALL-104 cell therapy (six injections), the right axillary node completely regressed but the other nodes remained unchanged. Two cell boosts, 1 week apart (see Table 2), were then administered: during this period of time, a significant improvement in P.B.K.'s clinical well-being was documented (MKPS=0) with complete regression of the axillary lymph node and >50% decrease in the inguinal lymph nodes and in the neck mass. At this time, a thoracic radiograph was negative for lymphadenopathy and pulmonary infiltrates.

TALL-104 cell therapy was ended at this point. At re-examination, 1 week later, new subcutaneous nodules were found on P.B.K.'s left hind and left front legs. The nodules were confirmed to be a recurrence by cytological examination of needle aspirates. Surgical removal of the nodules, followed by in vitro analysis of the susceptibility to TALL-104 cell lysis was not possible since, 2 days later, the lesions had regressed by >50%. At re-examination 2 weeks later, no nodular lesions were palpable on P.B.K. and no signs of disease were detected. A state of long-lasting CR was achieved, documented by the absence of clinical signs of relapse upon repeated abdominal ultrasounds and thoracic x-rays throughout the rest of P.B.K.'s life (14 months).

Unfortunately, seven months after achieving a CR, P.B.K. developed signs of chronic kidney failure, likely due to a severe urinary tract infection. The disease was stabilized for a few months using antibiotics and a low protein diet as supportive therapy, however, renal failure grew more severe and P.B.K. eventually died with a clinical picture of acute abdominal disease with ascites and bloody diarrhea. Necropsy revealed ischemic necrosis of the intestine (ultimate cause of death), but no macroscopic signs of MH. In particular, his spleen and liver, which are the classic sites of systemic MH [O. W. Schalm et al., Canine Practice, 5: 42–44 (1978); M. L. Schmidt et al., Vet. Quarterly, 15:117–120 (1993); P. F. Moore et al., Vet. Pathol., 23:1–10 (1986); A. Rosin et al., J. Am. Vet. Med. Assoc., 188:1041–1045 (1986); M. L. Wellman et al., J. Am. Vet. Med. Assoc., 187: 919–921 (1985)], appeared normal. Histological analysis (MH staining) was performed blindly by pathologists at the University of Pennsylvania Veterinary School of Medicine on formalin-fixed, paraffin-embedded necropsy samples of the dog's kidneys, bladder, liver, spleen, stomach, intestine, heart, lungs, and of mesenteric and mediastinal lymph nodes. No infiltrating malignant histiocytes were identified in any of these organs, and no evidence of other types of cancer were found at necropsy.

On the other hand, severe chronic lymphoplasmacytic tubulo-interstitial nephritis was found together with other organ changes, such as uremic pneumonitis and uremic gastritis, typically seen in severe kidney failure leading to uremia. Moreover, signs of thromboembolism were detected in the liver and spleen, and around the abdominal lymph nodes, consistent with a pathological diagnosis of thromboembolic disease, which has been described to be associated with renal failure (R. A. Greene et al., JAVMA, 182: 914–920 (1982); R. A. Greene, JAVMA, 186: 485–496 (1985)].

F.C. was the second dog with MH treated with TALL-104 cells (and CsA) (Table 3). Before cell therapy, the dog presented with multiple cutaneous nodules between pads and along metatarsus of the right hind leg with metastatic popliteal lymph node. Within 3 weeks from the first 5-day cycle of TALL-104 cells, the most proximal cutaneous lesions completely regressed while the more distal mass had only partially regressed and the popliteal lymph node had remained unchanged. A second 5-day cell cycle was then administered. In the following month, F.C. achieved a partial response (PR) (>50% reduction of cutaneous masses and popliteal lymph node) that lasted for 2 months (Table 3). Eventually, both the interdigital masses and lymph node grew back. A second PR was achieved following 2 monthly boostings with TALL-104 cells, and lasted about 6 months with stabilization of the cutaneous lesions. No signs of visceral disease were ever seen in this dog throughout cell therapy. When the lesions of the right hind leg started to progress again (19 months from start of cell therapy) the decision was made to suspend TALL-104 cell treatment. Chemotherapy (doxorubicin and dacarbazine, given to F.C. for 5 days, induced a PR (skin lesions and popliteal lymph node were reduced by $\geq 50\%$). Another 5-day TALL-104 cell cycle given 2 weeks later, resulted in a CR with complete disappearance of lesions. At the time of this writing F.C. has no evidence of cutaneous nor visceral disease (Table 3).

M.G. was diagnosed with MH in December 1995 and started TALL-104 cell treatment in the middle of January 1996 (Table 2). At that time the dog presented with cutaneous nodes around the mouth and left axillary lymphadenopathy (Table 1). Chest X-rays and abdominal ultrasound excluded intrathoracic and abdominal involvement, respectively. One month after one 5-day TALL-104 cell cycle a decrease in the cutaneous nodules and axillary lymph nodes started to be noticeable. After the first 2-day boost with TALL-104 cells, the left axillary lymphadenopathy completely regressed and the cutaneous nodules went down by more than 50% of their initial size. However, 1 month later, just before the second cell boosting was scheduled, new cutaneous nodules appeared along the muzzle. The dog received his second 2-day cell boost and, in the following month, the new cutaneous nodules completely regressed: a long-lasting CR was then achieved with no signs of cutaneous or visceral disease recurrence, as documented by clinical and strumental exams in follow-up visits. M.G remains disease-free at the time of preparation of this manuscript (16+ months, Table 3).

S.S. was immediately treated with TALL-104 cells at diagnosis in September 1996. At this time the dog had multiple subcutaneous nodules around the mouth, a skin lesion on the ventral abdomen as well as submandibular, left popliteal and prescapular lymph nodes. After the first 5-day TALL-104 cell cycle no changes were noted in any of the lesions and a second cell cycle was administered (Table 2); within 1 week from the last injection, all of the cutaneous lesions as well as the lymph nodes started to regress and a CR was achieved (Table 3). The dog is still in CR at the time of this writing (+9 months).

Unfortunately, no tumor specimens were available from the dogs during this study to test the development of specific anti-tumor immunity. However, experiments with other dogs in a phase I trial demonstrated the ability of their PBMC to recognize and kill their own tumor cells in vitro during the course of TALL-104 cell therapy. The induction of endogenous anti-tumor immunity upon passive transfer of TALL-104 cells was recently demonstrated in a murine model of syngeneic leukemia in which TALL-104-treated and cured mice were able to reject further leukemia cell challenges [A. Cesano et al., Cancer Res., 56: 4444–4452 (1996)].

That the complete remission achieved by the dogs treated as described herein was a consequence of TALL-104 cell treatment was indicated by the facts that a) the disease in P.B.K. was progressing under chemotherapy, and b) none of these three dogs received other drugs (aside from CsA) during and/or after completion of cell therapy.

It is unusual that the disease in one of the dogs (F.C.) did not systemically progress 22 months from the diagnosis. To our knowledge, no spontaneous remissions have ever been documented in dogs with MH; visceral disease universally develops in these dogs despite aggressive chemotherapy treatment. The complete remission achieved upon single agent TALL-104 cell therapy is considered significant.

EXAMPLE 5

Clinical Laboratory Changes and Toxicity

P.B.K. and F.C. exhibited mild vomiting (responsive to antiemetics) and diarrhea (treated with Lomotil) during cell treatment. These symptoms could be prevented in F.C. by premedication with an anti-histaminic. The other two dogs did not show any signs of clinical toxicity associated with TALL-104 cell injections. Blood chemscreens, run regularly on samples obtained during cell therapy, revealed no abnormalities. Discrete leukocytosis with neutrophilia was noted in P.B.K. during the second week of treatment and after the two cell boosts: the number of white blood cells reached a maximum of $21.7 \times 10^9$/L with 98% granulocytes, but returned to baseline levels 48 hours after halting the therapy. No hematological changes were seen in the other three dogs. No severe side effects, such as "capillary-leak syndrome," were observed in the dogs during TALL-104 cell treatment.

Because of the novelty of infusing human (xenogeneic) effector cells for treatment of canine malignancies, it was crucial in the present study to demonstrate not only the lack of acute toxicity in these animals, as an immediate consequence of TALL-104 cell infusion (+CsA), but also the lack of chronic tissue injury, resulting from the release of toxic cytokines and/or to a slow clearance of dying TALL-104 cells. Although laboratory findings showed no direct evidence of acute kidney toxicity during the course of cell therapy, the development in P.B.K. of severe chronic pyelonephritis a few months after systemic injection of TALL-104 cells raises the question of a causal relationship between CsA/cell therapy and the onset of nephritis. In this regard, P.B.K. had recurrent episodes of bacterial cystitis prior to the onset of evident renal disease with no alterations in kidney functions detectable during cell treatment. Kidney abnormalities were also absent in all long term survivors enrolled in our phase I clinical trial with TALL-104 cells with or without CsA [A. Cesano et al., Cancer Res., 56: 3021–3029 (1996)], and in the three dogs with MH (M.G., F.C., and S.S.) described in this study. In addition, no significant changes in kidney function were observed in long-term toxicity studies performed on healthy dogs and non-human primates who received multiple systemic TALL-104 cell injections. On the other hand, a high frequency of renal disease has been reported in a number of terrier breeds [K. Eriksen and J. Grondalen, J. Sm. Anim. Pract., 25: 489–501 (1984); C. A. Picut and R. M. Lewis, Kal. Kan. Forum., 8: 2–8 (1989)].

The histopathological changes noted on P.B.K.'s kidneys at the time of post mortem examination were not compatible with those found with CsA-associated nephrotoxicity or with autoimmune nephropathy. Renal biopsies of CsA-treated patients show an interstitial fibrosis with tubular atrophy [W. M. Bennett, Basic mechanisms and pathophysiology of cyclosporin nephrotoxicity. In: B. D. Kahan (ed.), Cyclosporine, Diagnosis, and Management of Associated Renal Injury, pp. 297–302, Grune and Stratton, Inc. Publishing, 1985]. Toxic tubulopathy, peritubular capillary congestion, arteriolopathy and a striped form of interstitial fibrosis with tubular atrophy may also be present [Bennet, cited above]. On the other hand, immunologically induced nephropathy is usually characterized by primary alterations of the glomeruli (membrane-proliferative glomerular-nephritis) [R. Berkow, Immunologically mediated renal diseases. In: The Merck Manual of Diagnosis and Therapy, 16th Edition, pp. 1677–1683. Merck Research Laboratories, 1992] which were absent in P.B.K.'s kidneys.

EXAMPLE 6

Correlation Between Laboratory Findings and Clinical Responses

Serum samples obtained from the dogs at various times pre-, during, and post-therapy, were evaluated for the presence of human cytokines (TNF-α, IFN-γ, TNF-β, and GM-CSF) possibly released by TALL-104 cells upon tumor cell interaction in vivo. Only human TFN-β levels were significantly elevated in the serum of the dogs during TALL-104 treatment (not shown). A correlation between clinical response to immunotherapy with LAK/IL-2 and sustained production of TNF has been reported [J.-Y. Blay et al., Cancer Res., 50: 2371–2374 (1990)]. The lack of significant IFN-γ, TNF-α, or GM-CSF levels in dogs' serum samples might be due to the lower production and/or metabolism of these cytokines or to different production kinetics.

An interesting observation in this study was the striking correlation between the dogs cell-mediated immune response (as measured in $^{51}$Cr-release assay against human NK-sensitive and NK-resistant targets) and clinical disease (FIGS. 1 and 2A–2C). In particular, the cytotoxic activity of P.B.K.'s PBMC against U937 (NK-sensitive) and TALL-106 (NK-resistant) cells was close to 0% before cell therapy (Nov. 28, 1994), high just at the time when the tumor nodules appeared and then regressed (Jan. 11, 1995), low 2 weeks later when CR was achieved (Jan. 25, 1995) (FIG. 1), and negative in the following months (not shown).

In the case of F.C., the correlation between cell-mediated immunity and disease progression/regression was even more evident because of the fluctuating course of his disease and the closer monitoring of his immunity (FIG. 2A): three picks of cytotoxic activity by F.C.'s PBMC against K562 cells were detected, the first during the initial PR, the second at the time of the first relapse and during the second PR, and the third at the time of the second relapse. In the periods of time between tumor regression (when the disease was stable) the cytotoxic activity of this dog's PBMC was close to 0%. Similar curves were seen in the case of M.G. and S.S. (FIGS. 2B and 2C) although their clinical courses were much simpler (CR without clinically detectable relapses).

EXAMPLE 7

Immune Response Against TALL-104 Cells

Figure 2A:
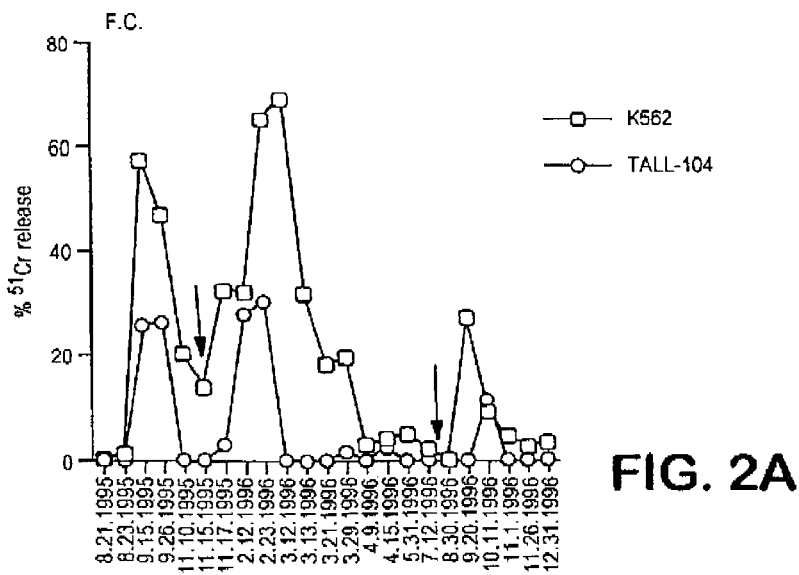
FIG. 2A is a line graph illustrating the cytotoxic activity of PBMC from canine patient "F.C." with malignant histiocytosis (MH) upon TALL-104 therapy. PBMC samples were harvested at the indicated dates before, during, and after TALL-104 therapy, and were tested for killer activity against K562 and TALL-104 cells in an 18 hour $^{51}$Cr release assay. The E:T ratio was 50:1. Arrows indicate the times of relapse, documented clinically.
Figure 2B:
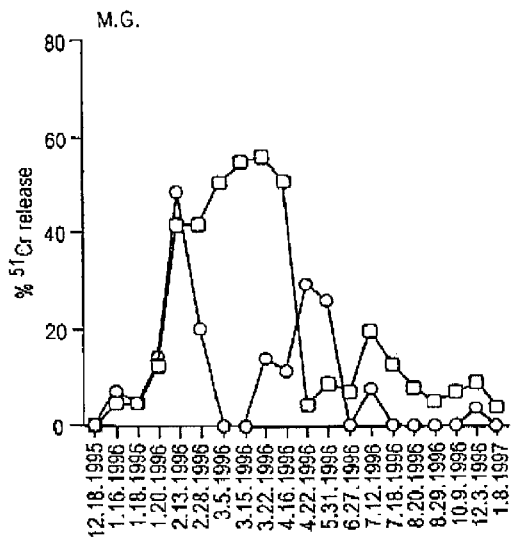
FIG. 2B is a line graph illustrating the cytotoxic activity of PBMC from canine patient "M.G." with MH upon TALL-104 therapy. The experiment was performed as in FIG. 2A.
Figure 2C:
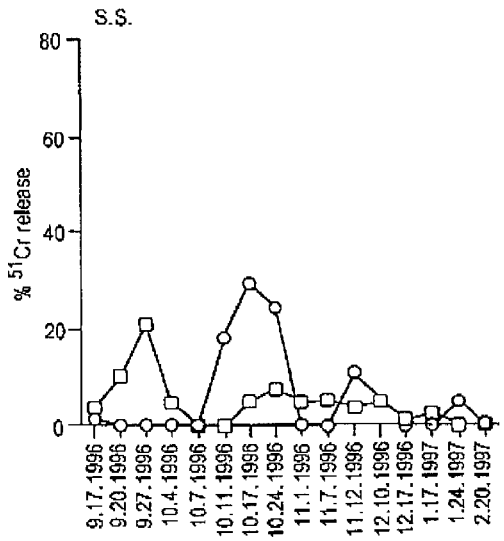
FIG. 2C is a line graph illustrating the cytotoxic activity of PBMC from canine patient "S.S." with MH upon TALL-104 therapy. The experiment was performed as in FIG. 2A.

No cellular immune responses against TALL-104 cells could be demonstrated in PBMC samples from P.B.K. at any interval during and after cell therapy, while specific CTL against TALL-104 cells were present in the PBMC of the other three dogs (FIGS. 2A–2C).

Despite the immunosuppressive regimen with CsA, P.B.K. and F.C. developed antibodies against TALL-104 cells between the second and third week of treatment. The same was true for M.G. and S.S. who did not receive any immunosuppressive drug. This humoral immune response in P.B.K., F.C., and M.G. was still present 1 year after completion of cell therapy. However, none of the TALL-104-reactive serum samples tested was able to inhibit TALL-104 cell tumoricidal activity, as determined by in vitro cytotoxicity assays against human and canine tumor target cell lines.

EXAMPLE 8

Detection of Circulating TALL-104 Cells

PCR amplification of the human mini-satellite region YNZ.22, performed on the PBMC of the TALL-104 cell treated dogs, documented the presence of TALL-104 cells in the circulation at various time points during therapy as well as their disappearance within 5 days after each injection. The lack of long-term persistence of TALL-104 cells in the circulation was confirmed by PCR analysis in each dog, months after completion of cell therapy.

EXAMPLE 9

Prevention of Recurrence MH in Canines

A canine patient diagnosed with MH is treated according to a conventional chemotherapeutic regimen, involving the intravenous administration of doxorubicin, cyclophosphamide, vincristine, dacarbazine, and L-asparaginase over the course of several weeks. Approximately one month following completion of the chemotherapeutic regimen, the patient is administered a course of treatment with modified TALL-104 cells, prepared essentially as described above in Example 3.

TALL-104 cells are γ-irradiated (40 Gy) and administered at the dose of $10^8$/kg in saline as an i.v. bolus over 30 minutes for five consecutive days. A cell boost is given one month following completion of the initial treatment and consists of 2 consecutive days of TALL-104 cell injections ($10^8$/kg, i.v.).

It is anticipated that the canine patients so treated will have complete remission of the MH.

EXAMPLE 10

Prevention of Recurrence of Lymphoma or Breast Carcinoma

A cancer patient diagnosed with lymphoma or carcinoma of the breast is treated by surgical removal of the tumor. Approximately six weeks following surgery, the patient is administered TALL-104 cells modified as described in Example 3. These cells are administered at the dose of $10^8$/kg in saline as an i.v. bolus over 30 minutes every other day for two weeks. A cell boost is given one month following completion of the initial treatment and consists of a single TALL-104 cell injection ($10^8$/kg, i.v.).

It is anticipated that in a cancer patient so treated no recurrence of the tumor will be observed.

EXAMPLE 11

Prevention of Recurrence of Osteosarcoma

A cancer patient diagnosed with osteosarcoma is treated surgically, followed by a course of chemotherapy. Approximately two weeks following chemotherapy, the patient is administered TALL-104 cells modified as described in Example 3. These cells are administered at the dose of $10^8$/kg in saline i.v. for five consecutive days. Monthly cell boosts may be administered at the above dose, for one to two days.

It is anticipated that in a patient so treated no recurrence of the cancer will be observed.

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. A method of treating cancer in a mammalian patient, comprising the step of:

administering to a mammalian cancer patient with a functional immune system an effective amount of TALL-104 cells ATCC Accession No. CRL 11386, which cells have been modified by stimulation in vitro by treatment with a cytokine and gamma irradiation at a dose suitable to irreversibly arrest cell proliferation but not interfere with the cytotoxic activity of the cells, said modified cells characterized by irreversibly arrested cell proliferation and non-MHC restricted cytotoxic activity, in the absence of an immunosuppressive agent.

2. The method according to claim 1, wherein said cytokine is selected from the group consisting of IL-2 and IL-12.

3. The method according to claim 1, wherein the patient is a veterinary patient.

4. The method according to claim 3, wherein the patient is a dog or cat.

5. The method according to claim 1, wherein the effective amount is between $10^7$ to about $10^8$ cells/kg/day.

6. The method according to claim 1, wherein the cells are administered intravenously.

7. The method according to claim 1, wherein the cells are administered via direct shunt.

8. The method according to claim 1, wherein the modified TALL-104 cells are administered to said patient on five consecutive days.

9. The method according to claim 1, further comprising administering cell boosts to the patient following said first administration step.

10. The method according to claim 1, wherein said patient has residual cancer and said administering step follows the completion of the primary cancer therapy.

11. The method according to claim 10 wherein said primary cancer therapy is surgery.

12. The method according to claim 10, wherein said primary cancer therapy is radiation therapy.

* * * * *

UNITED STATES PATENT AND TRADEMARK OFFICE
CERTIFICATE OF CORRECTION

PATENT NO. : 6,716,425 B1
DATED : April 6, 2004
INVENTOR(S) : Santoli et al.

It is certified that error appears in the above-identified patent and that said Letters Patent is hereby corrected as shown below:

Column 9,
Line 40, replace "Accu-Prep" with -- Accu-Prep$^{TM}$ --.
Line 43, replace "(both N1C-sensitive)" with -- (both NK-sensitive) --.
Line 54, replace "TNF-α" with -- TNF-β --.

Column 14,
Line 3, replace "TFN-β" with -- TNF-β --.

Signed and Sealed this

Fifteenth Day of November, 2005

JON W. DUDAS
*Director of the United States Patent and Trademark Office*